United States Patent [19]

Illig et al.

[11] Patent Number: 5,405,600

[45] Date of Patent: * Apr. 11, 1995

[54] X-RAY CONTRAST COMPOSITIONS CONTAINING FILM-FORMING MATERIALS

[75] Inventors: Carl R. Illig, Phoenixville; John L. Toner, Downingtown, both of Pa.

[73] Assignee: Sterling Winthrop Inc., New York, N.Y.

[*] Notice: The portion of the term of this patent subsequent to Jun. 7, 2011 has been disclaimed.

[21] Appl. No.: 104,744

[22] Filed: Aug. 11, 1993

Related U.S. Application Data

[63] Continuation-in-part of Ser. No. 877,690, May 1, 1992, abandoned.

[51] Int. Cl.⁶ .................... A61K 49/04; A61K 31/715
[52] U.S. Cl. ............................................ 424/5; 514/54; 514/57; 514/717; 514/941; 514/473; 514/942
[58] Field of Search ................... 424/5, 4; 514/54, 57, 514/717, 942, 941, 473; 568/580, 656

[56] References Cited

U.S. PATENT DOCUMENTS

| | | | |
|---|---|---|---|
| 2,613,172 | 10/1952 | Galler | 167/95 |
| 2,622,100 | 12/1952 | Newbery et al. | 260/612 |
| 2,832,722 | 8/1958 | Singher | 167/95 |
| 3,795,698 | 3/1974 | Soulal et al. | 260/471 R |
| 4,038,379 | 7/1977 | Elinov et al. | 424/4 |
| 4,069,306 | 1/1978 | Rothman | 424/4 |
| 4,120,946 | 10/1978 | Quemille et al. | 424/4 |
| 4,588,574 | 5/1986 | Felder et al. | 167/95 |
| 4,692,325 | 9/1987 | Kritzler | 424/4 |
| 5,019,370 | 5/1991 | Jay et al. | 424/4 |

FOREIGN PATENT DOCUMENTS

| | | |
|---|---|---|
| 1259565 | 9/1989 | Canada . |
| 1481943 | 5/1967 | France . |
| 55-127322 | 4/1980 | Japan . |

OTHER PUBLICATIONS

Wang et al, Yaoxne Xuebao, vol. 16, No. 8:610–617 (1981).

James et al, Pharm. Acta. Helvetiae, 47, 244–256 (1972).

*Primary Examiner*—Gary E. Hollinden
*Attorney, Agent, or Firm*—Fish & Richardson

[57] ABSTRACT

Disclosed are x-ray contrast compositions for oral or retrograde examination of the gastrointestinal tract comprising a polymeric material capable of forming a coating on the gastrointestinal tract and a nonionic x-ray producing agent in a pharmaceutically acceptable carrier; and methods for their use in diagnostic radiology of the gastrointestinal tract.

37 Claims, No Drawings

X-RAY CONTRAST COMPOSITIONS CONTAINING FILM-FORMING MATERIALS

This application is a continuation-in-part of application Ser. No. 07/877,690, filed May 1, 1992 now abandoned.

BACKGROUND OF THE INVENTION

1. Field of the Invention

This invention relates to an x-ray contrast composition for oral or retrograde administration to a mammal comprising a nonionic X-ray contrast producing agent and a polymeric film-forming material.

2. Reported Developments

Roentgenographic examination utilizing x-rays and computed tomography (hereinafter CT) scans of fractures and other conditions associated with the skeletal system is routinely practiced without the use of contrast agents. X-ray visualization of organs containing soft tissue, such as the gastrointestinal (hereinafter GI) tract, requires the use of contrast agents which attenuate x-ray radiation. D. P. Swanson et al in "Pharmaceuticals In Medical Imaging", 1990, MacMillan Publishing Company, provides an excellent background in medical imaging utilizing contrast agents and compositions therewith.

The most widely used contrast agents for the visualization of the GI tract is barium sulfate administered as a suspension orally or rectally as an enema. (See, for example, U.S. Pat. Nos. 2,659,690; 2,680,089; 3,216,900; 3,235,462; 4,038,379 and 4,120,946) Notwithstanding its relatively good contrast characteristics, negligible absorption from the GI tract following oral or rectal administration and speedy excretion from the body, barium sulfate has certain disadvantages. In the presence of intestinal fluids it lacks homogeneity and poorly adheres to mucus membranes which can result in poor x-ray images. In the colon, when administered as an enema, it flocculates and forms irregular clumps with fecal matter.

Iodinated organic compounds have also been used as contrast agents since the iodine atom is an effective x-ray absorber. They have the most versatility and are utilized in the widest variety of procedures. They are very absorptive of x-rays with which the iodine interacts and produce a so-called photoelectric effect which is a large magnification in contrast caused by the photons stopped in the iodine-containing medium. The magnification of contrast exceeds the level that would be expected from relative changes in density. Because of this magnification, relatively low concentrations of the contrast agent can be utilized. (For iodinated agents see, for example, U.S. Pat. Nos. 2,786,055; 3,795,698; 3,360,436; 3,574,718, 3,733,397; 4,735,795 and 5,047,228.)

The desiderata for an ideal GI contrast agent includes: good toxicological profile; the ability to fill the entire bowel/lumen and evenly coat the gut mucosa so that the presence of the bowel is detectable when the lumen is not distended; palatability and nonirritation to the intestinal mucosa; and passing through the GI tract without producing artifacts or stimulating vigorous intestinal peristalsis.

These requirements were addressed by many investigators and their efforts resulted in great improvements over the years. The requirement of evenly coating the gut mucosa with and sufficiently adhering thereto, a contrast agent to effectively cover the walls of the intestines proved to be rather difficult. Without meeting these requirements it is impossible to obtain x-ray pictures of high precision. To that end, the use of certain polymer additives were proposed as illustrated hereunder.

U.S. Pat. No. 4,069,306 discloses an x-ray contrast preparation which is said to adhere to the walls of body cavities. The preparation comprises a finely divided water-insoluble inorganic x-ray contrast agent and minute particles of a hydrophilic polymer which is insoluble in water but is water-swellable. The body cavity is supplied with such preparation suspended in water. The x-ray contrast agent is present in admixture with and/or enclosed in and/or adhered to said minute polymer particles.

U.S. Pat. No. 4,120,946 discloses a pharmaceutical composition for barium opacification of the digestive tract, comprising colloidal barium sulfate and a polyacrylamide in an aqueous vehicle. The polyacrylamide forms a viscous solution at low concentration which makes it possible to maintain the barium sulfate in suspension and at the same time permit good adherence of the preparation to the walls of the organ which it is desired to x-ray.

U.S. Pat. No. 5,019,370 discloses a biodegradable radiographic contrast medium comprising biodegradable polymeric spheres which carry a radiographically opaque element, such as iodine, bromine, samarium and erbium. The contrast medium is provided either in a dry or liquid state and may be administered intravenously, orally and intra-arterially.

Japanese Pat. Application No. 55-127322 discloses x-ray contrast compositions containing barium sulfate and a polymeric substance selected from carboxymethyl cellulose salts, propylene glycol alginate, cellulose sulfate polyacrylate, pectin and tragacanth gum. The polymeric substance is used to increase the viscosity of the compositions.

While these polymeric materials enhance attachment of the contrast agent used therewith to the walls of organs for better visualization thereof, they do not provide a polymeric coating thereon or prevent flocculation. As such, there is still a need for an improved x-ray imaging medium that uniformly coats the soft tissues subjected to diagnostic x-ray examination.

While these polymeric materials greatly enhance attachment of the contrast agent used therewith to the walls of organs for better visualization thereof, they do not provide a uniform coating thereon. As such, there is still a need for an improved x-ray imaging medium that uniformly coats the soft tissues subjected to diagnostic x-ray examination.

SUMMARY OF THE INVENTION

It is the object of the present invention to provide compositions for coating the gastrointestinal tract of mammals to form an effective radiopaque coating thereon by which diagnostic examination of the GI tract may be accomplished. To that end, a thin coating is formed on the inner surface of the GI tract effected by ingesting, prior to visualization by an x-ray emitting device, a polymeric film former, which has incorporated therein an x-ray contrast agent, capable of coating the GI tract. The removal of the coating occurs as a result of the normal turnover of cells, that is, within about 24 to 48 hours. Such compositions must meet several requirements: both the x-ray contrast agent and the film former must be nontoxic; must not contain leachable or digestible components that would deleteriously affect the patient; no components of the coating should be absorbed by, and pass through, the inner surface of the intestine; and the composition must be capable of forming a film in the pH range of from about 5 to about 8.

The object of the present invention is achieved by a composition comprising: an x-ray contrast agent; a polymeric material which is at least partially water soluble and contains polarizable or ionizable groups; and a divalent metal ion selected from the group consisting of $Mg^{++}$, $Ca^{++}$, $Zn^{++}$ and $Ba^{++}$ which potentiates the effect of the polymeric material as a film former on the mucosa of the GI tract.

The contrast agent, polymeric film former and the divalent metal ion are incorporated in a solid or liquid media for administration to a mammal for x-ray visualization of the GI tract.

The contrast agent utilized in the present invention is represented by the formula (I)

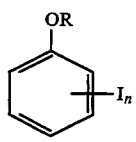
(I)

wherein R is a substituted or unsubstituted alkyl group containing from 2 to 8 carbon atoms, wherein said substituents are selected from the group consisting of $C_1$-$C_6$ alkyl, hydroxy and alkoxy; and n is 1 to 5.

Preferred contrast agents of the present invention have the formula:

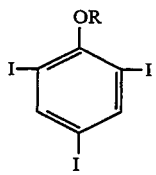

wherein R is a secondary alkyl group containing from 4 to 8 carbon atoms.

The most preferred contrast agent utilized by the present invention is the sec-octyl ether of 2,4,6-triiodophenol having the formula:

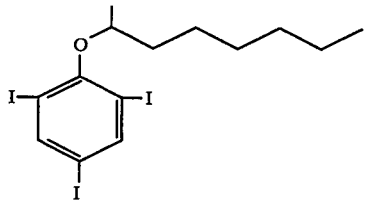

The compounds are readily synthesizable by methods known in the prior art. The compounds' desirable properties include: sufficient iodine content for producing adequate imaging; ability to coat the mucosal lining of the GI tract giving good imaging quality; and superior toxicological profile.

The compositions may be in the form of solids, dispersions, colloids or suspensoids, however, we prefer to use emulsions as the preferred embodiment.

The gist of the present invention resides in an x-ray contrast composition designed for depositing a thin, flexible film membrane onto the mucosal lining of the nutrient absorbing inner surface of the intestine of a patient to form a barrier between the nutrient absorbing inner surface and the content of the intestine, the flexible film membrane to remain bound to the mucosal lining until eliminated by normal cell turnover comprising based on w/v: of from about 0.001 to about 15% of a polymeric material capable of forming a film membrane on the gastrointestinal tract in the pH range of from about 5 to about 8, the polymeric material is selected from the group consisting of anionic polymers carrying negative charges in the ionized form, cationic polymers carrying positive charges in the ionized form and neutral polymers having polarizable electrons selected from the group consisting of oxygen, nitrogen, sulfur, fluoride, chloride, bromide and iodide in combination with of from about 0.001 to about 15% of a divalent cation to potentiate the binding of the flexible film membrane to the mucosal lining selected from the group consisting of $Ca^{++}$, $Mg^{++}$, $Zn^{++}$ and $Ba^{++}$; and of from about 0.001 to about 75% of a nonionic x-ray contrast producing agent having the formula

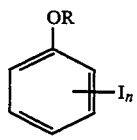
(I)

or a pharmaceutically acceptable salt thereof wherein R is a substituted or unsubstituted alkyl group containing from 2 to 8 carbon atoms, wherein said substituents are selected from the group consisting of $C_1$-$C_6$ alkyl, hydroxy and alkoxy; and n is 1 to 5; in a pharmaceutically acceptable carrier.

DETAILED DESCRIPTION OF THE INVENTION

The contrast agents utilized in the compositions of the present invention are slightly soluble in water, having a partition coefficient equal or greater than 10. This degree of solubility allows the formation of stable formulations in the form of dispersions, emulsions, suspensions when the formulations contain the requisite excipients. The term "stable" means that there is no separation of the ingredients contained in the compositions after oral or rectal administration thereof and during radiological examination of the GI tract. The slight solubility of the contrast agents in aqueous media permits diffusion of the contrast agents into the intestinal mucosa and secretions thereby forming a coating on the intestines. On the other hand, due to their slight solubility, the absorption of the contrast agent into the intestinal walls is minimal which reduces the possibility of toxic side effects.

Some of the contrast agents of the present invention can be prepared as described in U.S. Pat. No. 2,622,100, the disclosure of which is incorporated herein by reference. We, however, prefer utilizing the preparative methods described in the examples that follow.

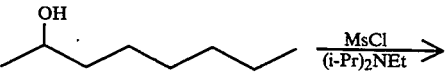

-continued

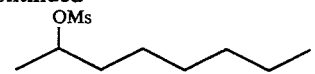

To 130 g (0.995 mol) of 2-octanol and 207 ml (1.19 mol, 1.2 equiv) of diisopropylethylamine in 1.5 L dichloromethane at 0° C. under a CaSO₄ drying tube was added dropwise 84.4 ml (1.09 mol, 1.1 equiv.) of methanesulfonyl chloride over 1 hour while keeping the internal temperature at less than 5° C. The faintly yellow solution was stirred at 0° C. for an additional 1.5 h. The cold reaction solution was then washed with 2×1 L ice-cold 1M HCl and 1 L of ice-cold H₂O and brine and dried over MgSO₄. The residue was filtered through Celite and concentrated in vacuo below 35° C. to afford 208 g of a yellow oil. The yellow oil was placed under high-vacuum for 2 h at 25° C. to give 205 g of yellow oil. NMR spectra confirmed the desired title-product having only trace amounts of solvents present.

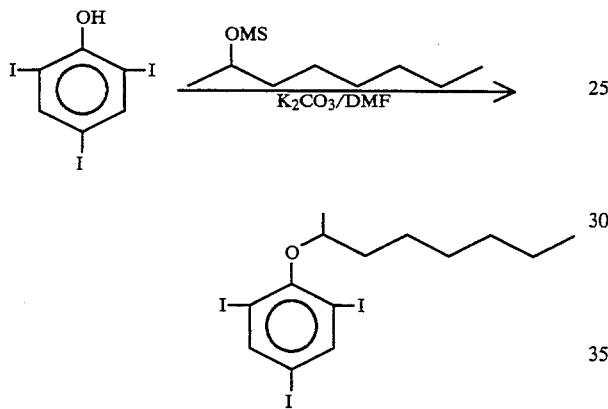

To a 5 L round bottom flask equipped with a mechanical stirrer was added, under nitrogen, 71.3 g (0.342 mol) of 2-mesyloxyoctane (obtained in A), 193 g (0.410 mol, 1.2 equiv) of 2,4,6-triiodophenol, 56.7 g (0.410 mol, 1.2 equiv.) of anhydrous potassium carbonate and 2.00 L of dimethylformamide (hereinafter DMF). The mixture was warmed slowly over one hour to reach a temperature of 55° C. to 60° C. and then stirred at 55° C. for 16 hours.

The temperature was raised to 65° C. and the mixture stirred for an additional 4 hours, then slowly cooled to room temperature and filtered through Celite to remove solids. The amber-colored DMF filtrate was extracted with 3×500 ml hexane to remove some of the product (first extract). TLC (25% EtOAc-hexane) indicated that the extract was the extremely pure title-product.

The DMF solution remaining after extraction with hexane was diluted with 9 L H₂O and 1 L of 1M NaOH. This mixture was extracted with 3×750 ml hexane (second extract). TLC showed that the extract was somewhat less pure than the first extract, but still only contained minor impurities.

The first extract and second extract were then separately washed with 2×500 ml of 1M NaOH, 500 ml of H₂O, 500 ml of saturated Na₂SO₃, 4×1 L H₂O, 1 L of brine and dried over Na₂SO₄.

Concentration in vacuo followed by high vacuum afforded from the first extract 65.5 g of a faintly yellow oil (33% yield). NMR spectra confirmed the extremely pure title-product containing no measurable amount of other materials, such as unreacted mesylate.

The second extract afforded 92.2 g (46% yield) of a light amber-colored oil. NMR spectra confirmed a reasonably pure product having only trace amounts of impurities, such as mesylate.

The 65.5 g of product obtained from the first extract was filtered through 500 g of silica eluting with 6 L of hexane to remove the trace of yellow color. Concentration in vacuo and under high vacuum and warming for 15 minutes afforded 64.7 g of the pure, colorless oil (99% recovery). NMR spectra confirmed the same very pure product as before.

The 92.2 g of product obtained from the second extract was subjected to the same procedure as the first extract. The product was found to be pure (98% recovery) without having a yellow color and without trace amounts of impurities, such as mesylate.

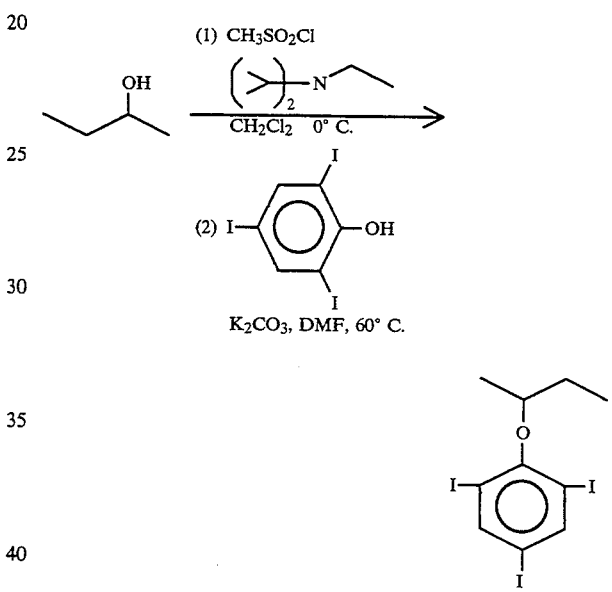

To a solution of 45.0 mmol of 2-butanol (4.1 ml) in dichloromethane at 0° C. was added 1.2 equiv. (9.4 ml) of diisopropylethylamine. After about 10 minutes, 1.1 equiv. (4.8 ml) of methanesulfonyl chloride was added slowly by syringe over about 10 min. The solution was stirred in an ice/water bath for 2.5 h, then poured over cold 5% HCl. The layers were separated and the organic layer was washed with cold 5% aqueous HCl and brine and dried over Na₂SO₄. The dried residue was dissolved in DMF (100 ml) and 50.0 mmol (23.6 g) of 2,4,6-triiodophenol was added which was followed by the addition of 50.0 mmol (6.9 g) of potassium carbonate. (The solution at this point turned dark and was difficult to stir). Stirring continued for 17 h. The solution was then cooled, filtered through Celite using DMF. The so-obtained DMF-containing solution was twice extracted with hexane, diluted with 200 ml of 0.1M aqueous NaOH and again extracted twice with hexane. The hexane extracts were combined and washed with 2×50 ml 1M NaOH, 2×50 ml H₂O and brine. The organic layer was dried over Na₂SO₄, filtered and the solvent removed in vacuo. Purification of the residue by flash column chromatography (silica, hexanes) gave 9.9 g of the title product as an oil.

An alternate method of making the compound of Example 2 is described in Example 3.

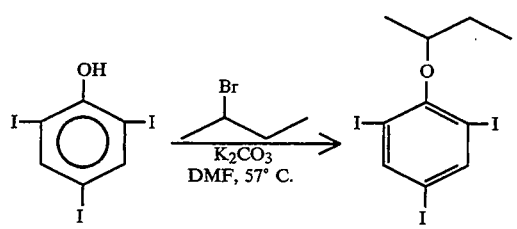

To a solution of 21.19 mmol (10.0 g) of 2,4,6-triiodophenol in 40 ml (0.5M) DMF at room temperature was added 2.0 equiv (4.6 ml) of 2-bromobutane and 2.0 equiv. (5.86 g) of potassium carbonate. The mixture was heated to 57° C. in an oil bath and stirred for 65 h. The mixture was then cooled, filtered through Celite by washing with DMF. The DMF-containing solution was extracted with hexane, diluted with 10% NaOH (100 ml) in H$_2$O, and extracted 3 times with hexane. The extracts were combined and washed twice with 1M NaOH, twice with H$_2$O and twice with brine. The organic layer was dried over Na$_2$SO$_4$, filtered and the solvent was removed in vacuo. Purification by flash column chromatography (hexanes, silica) yielded 10.83 g of the title product in the form of an oil.

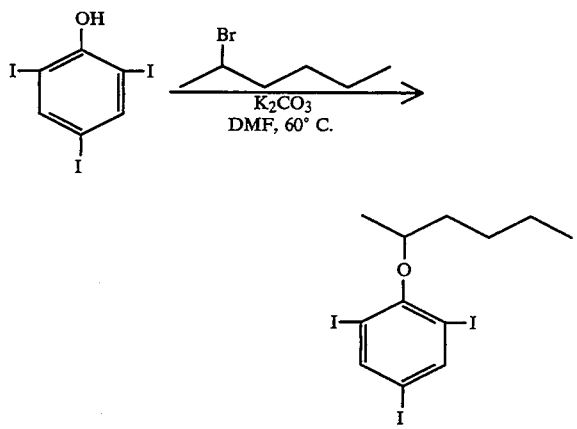

To a solution of 63.6 mmol (30 g) of 2,4,6-triiodophenol in 125 ml of DMF (0.5M) at room temperature was added 1.2 equiv. (10.8 ml) of 2-bromohexane and 1.5 equiv. (13.2 g) of potassium carbonate. The mixture was heated to 58° C. over 1.5 h, then stirred 40 h. The reaction mixture was filtered through Celite using DMF. The volume of DMF was reduced to 200 ml by evaporation in vacuo. The mixture was extracted twice with hexane, diluted with 500 ml of 10% NaOH in H$_2$O and extracted again with hexane 3 times. The hexane extracts were then combined and washed twice with 1M NaOH, twice with H$_2$O and once with brine. The organic layer was then dried over Na$_2$SO$_4$, filtered and the solvent was removed in vacuo. Flash column chromatography (hexanes, silica) yielded 31.5 g of the title compound in the form of an oil.

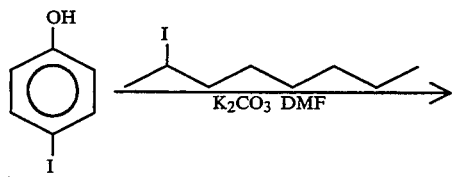

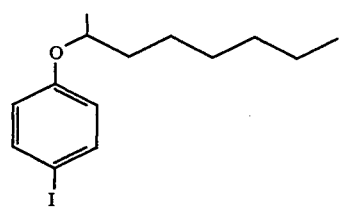

A mixture of 50.0 g (0.227 mol) of 4-iodophenol, 45.4 g (0.189 mol) of 2-iodooctane and 94.1 g (0.681 mol) potassium carbonate in 500 ml dry acetonitrile was heated to reflux under nitrogen and stirred for 20 h. The mixture was cooled and filtered through Celite and concentrated in vacuo. The brown residue was partitioned between 1 L hexanes and 500 ml 1M NaOH. The hexane layer was then washed with 1M NaOH (3×250 ml) saturated sodium sulfite (250 ml), water (250 ml) and brine (250 ml). The faintly yellow solution was dried over Na$_2$SO$_4$ and concentrated in vacuo to 34.3 g of a light yellow oil. The material in 60 ml of hexane was passed through a 600 g pad of silica gel eluting with 3% ethyl acetate-hexanes until just prior to elution of the yellow color. Concentration and warming under high vacuum afforded 26.9 g (43%) of product as a mobile colorless oil.

Other compounds of formula I may be prepared using the reaction techniques described in Examples 1 through 5 using appropriate starting materials and reagents. It is to be understood that all reaction conditions, including choice of solvents, reaction atmosphere, reaction temperature, duration of the experiment and workup procedures, are chosen to be conditions standard for that reaction, which should be readily recognized by one skilled in the art. It is understood by one skilled in the art of organic synthesis that the functionality present on portions of the educt molecule must be compatible with the reagents and reactions.

Starting materials, reagents and solvents can be obtained from chemical suppliers, such as Aldrich, Baker and Eastman Chemical Companies, or they may be prepared by techniques known in the prior art.

The polymers that were found to be suitable for forming a thin coating on the GI tract can be classified as anionic, cationic and neutral polymers, a description of which follows. U.S. Pat. No. 4,623,539, the disclosure of which is incorporated by reference, pertains to such polymers.

The contrast agent is incorporated in the polymeric material along with the divalent cation by any suitable techniques, such as by mixing, blending, precipitating or by enclosing the contrast agent into minute polymeric particles.

The contrast agent, polymeric material and divalent cation blend is then formulated for administration using physiologically acceptable carriers or excipients in a manner within the skill of the art. The contrast agent with the addition of pharmaceutically acceptable aids (such as surfactants and emulsifiers) and excipients may be suspended or partially dissolved in an aqueous medium resulting in a dispersion, solution, suspension or emulsion. Alternatively, the contrast agent, polymeric material and divalent cation may be formulated into a solid form, such as tablets or capsules.

Compositions

Compositions of the present invention comprise the following pharmaceutically acceptable components based on % w/v:

| | |
|---|---|
| Non-aqueous phase | 1-45 |
| Polymeric Material | 0.001-15 |
| Divalent Cation | 0.001-15 |
| Contrast Agent | 0.001-75 |
| Excipient | 0-20 |
| Aids (Surfactants/Emulsifiers) | 0.01-10 |
| Water | q.s. to 100 |

The nonaqueous phase comprises vegetable oils such as safflower oil; non-metabolizing fat substituents, such as Simpless; fluorinated hydrocarbons, such as perfluorodecaline; mineral oil and simethicone.

The contrast agent is selected from the group of compounds of formula I, preferably compounds where R is an alkyl group containing from 4 to 8 carbon atoms.

Excipients advantageously used in the formulations include viscosity mediating and stabilizing agents, such as microcrystalline cellulose, ethylcellulose, hydroxypropyl methylcellulose and gum arabic. Physiologically acceptable substances may also be included, such as sodium citrate, sodium chloride, therapeutic substances, antacid substances and flavoring agents. The inclusion of antimicrobial/antiseptic agents such as methyl parahydroxybenzoate, ethyl parahydroxybenzoate, propyl parahydroxybenzoate, benzoic acid or sorbic acid may also be desirable in some formulations.

As known by those skilled in the art, surfactants or emulsifiers can reduce the interfacial tension between two immiscible phases, i.e., oil-in-aqueous medium. These agents can be used alone or in combination with other emulsifying agents and surfactants. For example, Dow Corning Medical Antifoam AF, which is a composition of 30% w/v polydimethylsiloxane and silica aerogel, 14% w/v stearate emulsifiers and 0.075% w/v sorbic acid, the balance being water, may be used by itself. Intralipid, which is an emulsion of fatty acids needs the presence of a suspending agent for it to form an acceptable emulsion with contrast agents of the present invention. The amount of such surfactants may be in the range of from 0.01 to 5% w/v of the aqueous formulations, although the amount, in general, is kept as low as possible, preferably in the range of 0.05 to 2% w/v. The surface active agents may be cationic, anionic, nonionic, zwitterionic or a mixture of two or more of these agents.

Suitable cationic surfactants include cetyl trimethyl ammonium bromide. Suitable anionic agents include sodium lauryl sulphate, sodium heptadecyl sulphate, alkyl benzenesulphonic acids and salts thereof, sodium butylnapthalene sulfonate, and sulphosuccinates. Zwitterionic surface active agents are substances that when dissolved in water they behave as diprotic acids and, as they ionize, they behave both as a weak base and a weak acid. Since the two charges on the molecule balance each other out they act as neutral molecules. The pH at which the zwitterion concentration is maximum is known as the isoelectric point. Compounds, such as certain amino acids having an isoelectric point at the desired pH of the formulations of the present invention are useful in practicing the present invention.

In preparing the formulations of the present invention we prefer to use nonionic emulsifiers or surface active agents which, similarly to the nonionic contrast agents, possess a superior toxicological profile to that of anionic, cationic or zwitterionic agents. In the nonionic emulsifying agents the proportions of hydrophilic and hydrophobic groups are about evenly balanced. They differ from anionic and cationic surfactants by the absence of charge on the molecule and, for that reason, are generally less irritant than the cationic or anionic surfactants. Nonionic surfactants include carboxylic esters, carboxylic amides, ethoxylated alkylphenols and ethoxylated aliphatic alcohols.

One particular type of carboxylic ester nonionic surface active agents are the partial, for example mono-, esters formed by the reaction of fatty and resin acids, for example of about 8 to about 18 carbon atoms, with polyalcohols, for example glycerol, glycols such as mono-, di-, tetra- and hexaethylene glycol, sorbitan, and the like; and similar compounds formed by the direct addition of varying molar ratios of ethylene oxide to the hydroxy group of fatty acids.

Another type of carboxylic esters is the condensation products of fatty and resin partial acids, for example mono-, esters ethylene oxide, such as fatty or resin acid esters of polyoxyethylene sorbitan and sorbitol, for example polyoxyethylene sorbitan, mono-tall oil esters. These may contain, for example, from about 3 to about 80 oxyethylene units per molecule and fatty or resin acid groups of from about 8 to about 18 carbon atoms. Examples of naturally occurring fatty acid mixtures which may be used are those from coconut oil and tallow while examples of single fatty acids are dodecanoic acid and oleic acid.

Carboxylic amide nonionic surface active agents are the ammonia, monoethylamine and diethylamides of fatty acids having an acyl chain of from about 8 to about 18 carbon atoms.

The ethoxylated alkylphenol nonionic surface active agents include various polyethylene oxide condensates of alkylphenols, especially the condensation products of mono-alkylphenols or dialkylphenols wherein the alkyl group contains about 6 to about 12 carbon atoms in either branched chain or particularly straight chain configuration, for example, octyl cresol, octyl phenol or nonyl phenol, with ethylene oxide, said ethylene oxide being present in amounts equal to from about 5 to about 25 moles of ethylene oxide per mole of alkylphenol.

Ethoxylated aliphatic alcohol nonionic surface active agents include the condensation products of aliphatic alcohols having from about 8 to 18 carbon atoms in either straight chain or branched chain configuration, for example oleyl or cetyl alcohol, with ethylene oxide, said ethylene oxide being present in equal amounts from about 30 to about 60 moles of ethylene oxide per mole of alcohol.

Preferred nonionic surface active agents include:
(a) Sorbitan esters (sold under the trade name Span) having the formula:

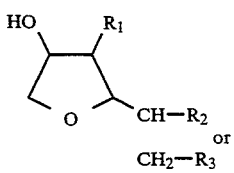

wherein
$R_1 = R_2 = OH, R_3 = R$ for sorbitan monoesters, $R_1=OH, R_2=R_3=R$ for sorbitan diesters,
$R_1=R_2=R_3=R$ for sorbitan triesters,
where $R=(C_{11}H_{23})COO$ for laurate, $(C_{17}H_{33})COO$ for oleate, $(C_{15}H_{31})COO$ for palmitate, $(C_{17}H_{35})COO$ for stearate;

(b) Polyoxyethylene alkyl ethers (i.e. Brijs) having the formula:

$$CH_3(CH_2)_x(O-CH_2-CH_2)_yOH$$

where (x+1) is the number of carbon atoms in the alkyl chain, typically:

| 12 lauryl | (dodecyl) |
|---|---|
| 14 myristyl | (tetradecyl) |
| 16 cetyl | (hexadecyl) |
| 18 stearyl | (octadecyl) | and y is the number of ethylene oxide groups in the hydrophilic chain, typically 10-60;

(c) Polyoxyethylene sorbitan fatty acid esters, sold under the trade names of Polysorbates 20, 40, 60, 65, 80 & 85; and (d) Polyoxyethylene stearates, such as:
poly(oxy-1,2-ethanediyl),α-hydro-ω-hydroxy-octadecanoate;
polyethylene glycol monostearate; and
poly(oxy-1,2-ethanediyl)-α-(1-oxooctadecyl)-ω-hydroxy-polyethylene glycol monostearate.

The film former polymeric materials used in accordance with the present invention include anionic polymers, cationic polymers and neutral polymers.

I. Anionic Polymers

The anionic polymers carry negative charges in the ionized form and are capable of binding to cell surfaces mainly by electrostatic forces. Suitable anionic polymers include the following:

$$R-O-\overset{\overset{O}{\|}}{\underset{\underset{O}{\|}}{S}}-O-M^{++}, \quad R-\overset{\overset{O}{\|}}{C}-O-M^{++},$$

$$R-O-R-\overset{\overset{O}{\|}}{C}-O-M^{++}$$

wherein
R is the polymeric chain;

$$-O-\overset{\overset{O}{\|}}{\underset{\underset{O}{\|}}{S}}-O- \quad \text{and} \quad \overset{\overset{O}{\|}}{C}-O-$$

are anionic ligands; and
$M^{++}$ is a divalent cation.

Specific anionic polymers useful in the practice of the present invention include:

(1) Sulfated polysaccharides of the formula:

$$R-O-\overset{\overset{O}{\|}}{\underset{\underset{O}{\|}}{S}}-O-M^{++}$$

wherein
R is 3,6-anhydro-D-galactose linked through C-4 to D-galactose; (kappa carrageenan) α-D-galactose units (1–3) linked; (lambda carrageenan) D-galactose 3,6-anhydro-D-galactose; (iota carrageenan) D-galactose 3,6-anhydro-L-galactose: (Agar—Agar) D-galactose 3,6-anhydro-D-galactose; (Furcellaren) D-glucopyranose; (Laminarin sulfate) Galactan; and (Galactan sulfate) Galactosaminoglucuronans (Chondroitin sulfates); and
$M^{++}$ is $Mg^{++}$, $Ca^{++}$, $Zn^{++}$, $Ba^{++}$ or mixtures thereof.

(2) Carboxylated polysaccharides of the formula:

$$R-\overset{\overset{O}{\|}}{C}-O-M^{++}$$

wherein
R is D-galacturonoglycan; and (Pectin) anhydro-D-mannuronic acid and anhydro-L-guluronic acid (Algin) residues; and
$M^{++}$ is $Mg^{++}$, $Ca^{++}$, $Zn^{++}$, $Ba^{++}$ or mixtures thereof.

(3) Cellulose derivatives of the formulae:

$$R'-O-R-O-\overset{\overset{O}{\|}}{\underset{\underset{O}{\|}}{S}}-O-M^{++},$$

$$R'-O-\overset{\overset{O}{\|}}{C}-R-O-\overset{\overset{O}{\|}}{\underset{\underset{O}{\|}}{S}}-O-M^{++} \text{ and}$$

$$R''-\overset{\overset{O}{\|}}{C}-R-\overset{\overset{O}{\|}}{C}-O-M^{++}$$

wherein
R is an anhydroglucose residue;
R' is $CH_3$, $C_2H_5$ or $C_3H_7$;
R'' is $CH_3$ or $C_2H_5$; and
$M^{++}$ is $Mg^{++}$, $Ca^{++}$, $Zn^{++}$, $Ba^{++}$ or mixtures thereof.

Examples of cellulose derivatives include: sodium ethylcellulose sulfate, sodium cellulose acetate sulfate and sodium carboxymethyl cellulose.

(4) Sulfated, sulfonated or carboxylated synthetic polymers of the formula:

$$R-\overset{\overset{O}{\|}}{\underset{\underset{O}{\|}}{S}}-O-M^{++}, \quad R-O-\overset{\overset{O}{\|}}{\underset{\underset{O}{\|}}{S}}-O-M^{++} \text{ and } R-\overset{\overset{O}{\|}}{C}-O-M^{++}$$

wherein
R is an aliphatic or aromatic hydrocarbon, such as polystyrene, poly(sulfon) resin or carboxylated (poly) vinyl; and
$M^{++}$ is $Mg^{++}$, $Ca^{++}$, $Zn^{++}$, $Ba^{++}$ or mixtures thereof.

II Cationic Polymers

The cationic polymers carry positive charges in the ionized form. Suitable polymers for practicing the present invention include: dermatan sulfate, keratosulfate, hyaluronic acid, heparin and chitin.

III Neutral Polymers

Neutral polymers having polarizable electrons such as oxygen, nitrogen, sulfur, fluoride, chloride, bromide and iodide are also suitable for practicing the present invention. In the presence of a cation, such as $Mg^{++}$, $Ca^{++}$, $Zn^{++}$ or $Ba^{++}$, the polymers are partially polarized thereby providing intermolecular interactions between the polymer and the intestinal wall. Examples of these polymers include:

(a) Polysaccharides, such as starch, glycogen, glucan, fructans, mannans, galactomannas, glucomannans, galactans, xylans, glycuranans, dextran and starch amylose;

(b) Cellulose derivatives, such as methylcellulose, hydroxyethylcellulose, ethylhydroxyethyl cellulose, hydroxypropyl methylcellulose and hydroxypropyl cellulose; and (c) Synthetic polymers, such as polyvinylpyrrolidone, polyvinyl alcohol and ethylene oxide polymers.

Exemplary formulations of the present invention are as shown:

| Example 6 | |
|---|---|
| Compound of Example 1 (114 mg I/ml) | 2.50 g (17.5% w/v) |
| Dow Corning Med. Antifoam AF emulsion | 3.50 g (35% w/v) |
| Galactan sulfate | 0.5 g (5% w/v) |
| Calcium lactate | 0.5 g (5% w/v) |
| Purified Water | q.s. to 10 ml |
| Example 7 | |
| Compound of Example 1 (114 mg I/ml) | 2.50 g (17.5% w/v) |
| Safflower Oil | 2.00 g (20% w/v) |
| Tween-21 | 0.25 g (2.5% w/v) |
| Hydroxypropyl methylcellulose (4,000 cPs) | 2.50 g of 2% solution |
| Calcium lactate | 0.2 g (2% w/v) |
| Purified Water | q.s. to 10 ml |
| Example 8 | |
| Compound of Example 1 (114 mg I/ml) | 2.50 g (17.5% w/v) |
| Mineral Oil | 0.50 g (5% w/v) |
| Heparin | 0.25 g (2.5% w/v) |
| Tween-21 | 0.25 g (2.5% w/v) |
| Calcium lactate | 0.25 g (2.5% w/v) |
| Purified Water | q.s. to 10 ml |
| Example 9 | |
| Compound of Example 1 (114 mg I/ml) | 2.50 g (17.5% w/v) |
| Simplesse 100 (Nutrasweet Co.) | 3.00 g (30% w/v) |
| Calcium lactate | ~0.5 g (5% w/v) |
| Hydroxypropyl methylcellulose (4000 cPs) | 2.50 g of 2% solution |
| Purified Water | q.s. to 10 ml |

The dosages of the contrast agent used according to the method of the present invention will vary according to the precise nature of the contrast agent used. Preferably, however, the dosage should be kept as low as is consistent with achieving contrast enhanced imaging. By employing as small amount of contrast agent as possible, toxicity potential is minimized. For most contrast agents of the present invention dosages will be in the range of from about 0.1 to about 16.0 g iodine/kg body weight, preferably in the range of from about 0.5 to about 6.0 g iodine/kg of body weight, and most preferably, in the range of from about 1.2 to about 2.0 g iodine/kg body weight for regular x-ray visualization of the GI tract. For CT scanning the contrast agents of the present invention will be in the range of from about 1 to about 600 mg iodine/kg body weight, preferably in the range of from about 20 to about 200 mg iodine/kg body weight, and most preferably in the range of from about 40 to about 80 mg iodine/kg body weight.

The concentration of the contrast agent should be in the range of from about 0.001% w/v to about 75% w/v of the formulation, preferably from about 0.05% w/v to about 50% v/v and most preferably of from about 0.1% w/v to about 20% w/v.

The concentration of the film forming polymeric material depends on the particular polymer used, however, it should be in the range of 0.001 to about 15% w/v or higher in combination with a divalent substance, such as calcium lactate, having a concentration range of 0.001 to 15% w/v. The use of less than about 0.001% of a divalent cation was found to be less than satisfactory in forming a film on the mucosa of the intestines. Dosage level of the polymeric material may be in the range of from about 2 to about 15 g/kg body weight or higher.

The compositions of the present invention possess very good adherence to the walls of the gastrointestinal tract by forming an essentially uniform coating thereon.

The invention, having been fully described, it will be apparent to one skilled in the art that changes and modifications can be made thereto without departing from the spirit and scope thereof.

What is claim is:

1. An x-ray contrast composition designed for depositing a thin, flexible film membrane onto the mucosal lining of the nutrient absorbing inner surface of the intestine of a patient to form a barrier between said nutrient absorbing inner surface and the content of said intestine, said flexible film membrane to remain bound to said mucosal lining until eliminated by normal cell turnover comprising based on w/v:

(a) of from about 0.001 to about 15% of a polymeric material capable of forming a film membrane on the gastrointestinal tract in the pH range of from about 5 to about 8, said polymeric material is selected from the group consisting of
anionic polymers carrying negative charges in the ionized form, cationic polymers carrying positive charges in the ionized form, and neutral polymers having polarizable electrons selected from the group consisting of oxygen, nitrogen, sulfur, fluoride, chloride, bromide and iodide in combination with (b) of from about 0.001 to about 15% of a divalent cation to potentiate the binding of said flexible film membrane to said mucosal lining selected from the group consisting of $Ca^{++}$, $Mg^{++}$, $Zn^{++}$ and $Ba^{++}$; and (c) of from about 0.001 to about 75% of a nonionic x-ray contrast producing agent having the formula

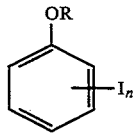

or a pharmaceutically acceptable salt thereof wherein R is a substituted alkyl group containing from 2 to 8 carbon atoms wherein said substituent is saturated $C_1$–$C_6$ alkyl; and n is 1 to 5; in a pharmaceutically acceptable carrier.

2. The x-ray contrast composition of claim 1 wherein said pharmaceutically acceptable carrier is a liquid.

3. The x-ray contrast composition of claim 1 wherein said pharmaceutically acceptable carrier is a solid.

4. The x-ray contrast composition of claim 1 wherein said polymeric material is anionic having the formula:

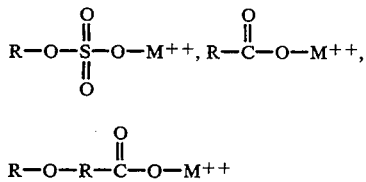

wherein
R is the polymeric chain;

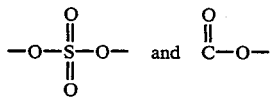

are anionic ligands; and
M++ is a divalent cation.

5. The x-ray contrast composition of claim 4 wherein said anionic polymeric material is a sulfated polysaccharide having the formula:

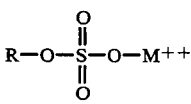

wherein
R is 3,6-anhydro-D-galactose linked through C-4 to D-galactose; (kappa carrageenan) α-D-galactose units (1-3) linked; (lambda carrageenan) D-galactose 3,6-anhydro-D-galactose; (iota carrageenan) D-galactose 3,6-anhydro-L-galactose: (Agar—Agar) D-galactose 3,6-anhydro-D-galactose; (Furcellaren) D-glucopyranose; (Laminarin sulfate) Galactan; and (Galactan sulfate) Galactosaminoglucuronans (Chondroitin sulfates); and
M++ is Mg++, Ca++, Zn++, Ba++ or a mixture thereof 6. The x-ray contrast composition of claim 4 wherein said anionic polymeric material is a carboxylated polysaccharide having the formula:

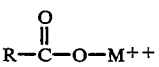

wherein
R is D-galacturonoglycan; and (Pectin) anhydro-D-mannuronic acid and anhydro-L-guluronic acid (Algin) residues; and
M++ is Mg++, Ca++, Zn++, Ba++ or a mixture thereof.

7. The x-ray contrast composition of claim 4 wherein said anionic polymeric material is a cellulose derivative of the formula:

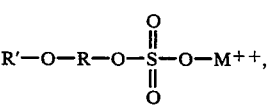

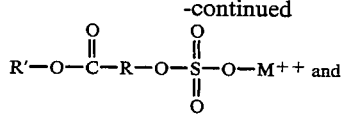

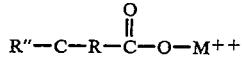

wherein
R is an anhydroglucose residue;
R' is CH₃, C₂H₅ or C₃H₇;
R'' is CH₃ or C₂H₅; and
M++ is Mg++, Ca++, Zn++, Ba++ or a mixture thereof.

8. The x-ray contrast composition of claim 7 wherein said cellulose derivative is selected from the group consisting of sodium ethylcellulose sulfate, sodium cellulose acetate sulfate and sodium carboxymethylcellulose.

9. The x-ray contrast composition of claim 1 wherein said anionic polymeric material is a sulfated, sulfonated or carboxylated synthetic polymer having the formula:

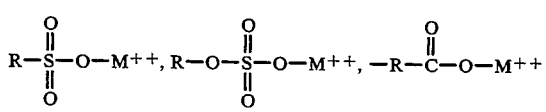

wherein
R is an aliphatic or aromatic hydrocarbon; and
M++ is Mg++, Ca++, Zn++, Ba++ or a mixture thereof.

10. The x-ray contrast composition of claim 1 wherein said polymeric material is cationic selected from the group consisting off dermatan sulfate, keratosulfate, hyaluronic acid, heparin and chitin.

11. The x-ray contrast composition of claim 1 wherein said polymeric material is a polysaccharide.

12. The x-ray contrast composition of claim 11 wherein said polysaccharide is selected from the group consisting of starch, glycogen, glucan, fructans, mannans, galactomannans, flucomannas, galactans, xylans, glycuranans, dextran and starch amylose.

13. The x-ray contrast composition of claim 1 wherein said polymeric material is a cellulose derivative.

14. The x-ray contrast composition of claim 13 wherein said cellulose derivative is selected from the group consisting of methylcellulose, hydroxyethyl cellulose, ethylhydroxyethyl cellulose and hydroxypropyl cellulose.

15. The x-ray contrast composition of claim 1 wherein said polymeric material is polyvinylpyrrolidone, polyvinyl alcohol or an ethylene oxide polymer.

16. The x-ray contrast composition of claim 1 in an aqueous dispersion.

17. The x-ray contrast composition of claim 1 in the form of an emulsion.

18. The x-ray contrast composition of claim 1 wherein said pharmaceutical carrier contains at least one surfactant.

19. The x-ray contrast formulation of claim 18 wherein said surfactant is cationic.

20. The x-ray contrast formulation of claim 18 wherein said surfactant is anionic.

21. The x-ray contrast formulation of claim 18 wherein said surfactant is zwitterionic.

22. The x-ray contrast formulation of claim 18 wherein said surfactant is nonionic.

23. The x-ray contrast formulation of claim 19 wherein said cationic surfactant is selected from the group consisting of cetyl trimethyl ammonium bromide and dodecyl dimethyl ammonium bromide.

24. The x-ray contrast formulation of claim 20 wherein said anionic surfactant is selected form the group consisting of sodium lauryl sulfate, sodium heptadecyl sulphate, an alkyl benzene sulphonic acid, sodium butylnaphthalene sulfonate and sulphosuccinate.

25. The x-ray contrast formulation of claim 22 wherein said nonionic surfactant is selected from the group consisting of carboxylic esters, carboxylic amides, ethoxylated alkylphenols and ethoxylated aliphatic alcohols, sorbitan esters, polyoxyethylene alkyl ethers and polyoxyethylene sorbitan fatty acid esters.

26. A method of carrying out x-ray examination of the gastrointestinal tract of a patient, said method comprises the oral or rectal administration to the patient an x-ray contrast composition designed for depositing a thin, flexible film membrane onto the mucosal lining of the nutrient absorbing inner surface of the intestine of a patient to form a barrier between said nutrient absorbing inner surface and the content of said intestine, said flexible film membrane to remain bound to said mucosal lining until eliminated by normal cell turnover comprising based on w/v:
(a) of from about 0.001 to about 15% of a polymeric material capable of forming a film membrane on the gastrointestinal tract in the pH range of from about 5 to about 8, said polymeric material selected from the group consisting of
anionic polymers carrying negative charges in the ionized form, cationic polymers carrying positive charges in the ionized form, and neutral polymers, having polarizable electrons selected from the group consisting of oxygen, nitrogen, so-sulfur, fluoride, chloride, bromide and iodide, in combination with
(b) of from about 0.001 to about 15% of a divalent cation to potentiate the binding of said flexible film membrane to said mucosal lining selected from the group consisting of $Ca^{++}$, $Mg^{++}$, $Zn^{++}$ and $Ba^{++}$; and
(c) of from about 0.001 to about 75% of a nonionic x-ray contrast producing agent having the formula

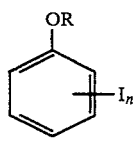

or a pharmaceutically acceptable salt thereof wherein R is a substituted alkyl group containing from 2 to 8 carbon atoms wherein said substituent is saturated $C_1$–$C_6$ alkyl; and n is 1 to 5; in a pharmaceutically acceptable carrier.

27. The method of claim 26 wherein the amount of contrast agent administered to said patient is in the range of from about 0.1 to about 16.0 g iodine/kg body weight for regular x-ray visualization of the gastrointestinal tract.

28. The method of claim 26 wherein the amount of contrast agent administered to said patient will be in the range of from about 1 to 600 mg iodine/kg body weight for CT scan visualization of the gastrointestinal tract.

29. The method of claim 26 wherein said x-ray contrast agent is in the form of an emulsion.

30. The method of claim 26 wherein said pharmaceutically acceptable carrier contains at least one surfactant.

31. The method of claim 30 wherein said surfactant is cationic.

32. The method of claim 30 wherein said surfactant is anionic.

33. The method of claim 30 wherein said surfactant is zwitterionic.

34. The method of claim 30 wherein said surfactant is nonionic.

35. The method of claim 31 wherein said cationic surfactant is selected from the group consisting of cetyl trimethyl ammonium bromide and dodecyl dimethyl ammonium bromide.

36. The method of claim 32 wherein said anionic surfactant is selected from the group consisting of sodium lauryl sulfate; sodium heptadecyl sulphate, an alkyl benzene sulphonic acid, sodium butylnaphthalene sulfonate and sulphosuccinates.

37. The method of claim 34 wherein said nonionic surface active agent is selected from the group consisting of carboxylic esters, carboxylic amides, ethoxylated alkylphenols and ethoxylated aliphatic alcohols, sorbitan esters, polyoxyethylene alkyl ethers and polyoxyethylene sorbitan fatty acid esters.

* * * * *